United States Patent [19]

Greenfield et al.

[11] Patent Number: 5,895,762
[45] Date of Patent: Apr. 20, 1999

[54] APPARATUS AND METHOD FOR HANDLING FLUID SAMPLES OF BODY MATERIALS

[75] Inventors: Walter Greenfield, Scarsdale, N.Y.; Mark J. Chiappetta, Sandy Hook; Todd M. DeMatteo, Farmington, both of Conn.

[73] Assignee: DiaSys Corporation, Waterbury, Conn.

[21] Appl. No.: 08/813,792

[22] Filed: Mar. 6, 1997

Related U.S. Application Data

[60] Provisional application No. 60/014,096, Mar. 26, 1996.

[51] Int. Cl.$^6$ .................. G01N 35/00; G01N 35/08; G01N 1/00; B01L 3/02
[52] U.S. Cl. .................. 436/43; 436/46; 436/52; 436/165; 422/58; 422/68.1; 422/81; 422/100; 422/101; 422/102; 73/864.02; 73/864.03; 73/864.74; 73/864.91
[58] Field of Search .................. 435/4; 436/46, 436/52, 165, 179, 180, 43; 422/58, 68.1, 81, 100, 101, 102; 356/246; 359/396, 398; 73/864.03, 864.02, 864.74, 864.91

[56] References Cited

U.S. PATENT DOCUMENTS

| | | | |
|---|---|---|---|
| 3,352,280 | 11/1967 | Hughes et al. | |
| 3,902,971 | 9/1975 | Fletcher et al. | 195/103.5 R |
| 4,025,393 | 5/1977 | Hirschfeld | 195/103.5 M |
| 4,034,700 | 7/1977 | Bassett et al. | 118/2 |
| 4,804,267 | 2/1989 | Greenfield | 356/335 |
| 4,847,208 | 7/1989 | Bogen | 436/174 |
| 4,963,498 | 10/1990 | Hillman et al. | 436/69 |
| 5,225,163 | 7/1993 | Andrews | 422/61 |
| 5,248,480 | 9/1993 | Greenfield et al. | 422/68.1 |
| 5,258,285 | 11/1993 | Ægidius | 435/8 |
| 5,300,779 | 4/1994 | Hillman et al. | 250/341 |
| 5,302,348 | 4/1994 | Cusack et al. | 422/73 |
| 5,312,731 | 5/1994 | Engström | 435/32 |
| 5,372,946 | 12/1994 | Cusak et al. | 436/69 |
| 5,393,494 | 2/1995 | Greenfield et al. | |
| 5,403,735 | 4/1995 | Maruhashi et al. | 435/240.1 |

*Primary Examiner*—Ponnathapura Achutamurthy
*Assistant Examiner*—P. Ponnaluri
*Attorney, Agent, or Firm*—St. Onge Steward Johnston & Reens, LLC

[57] ABSTRACT

A system for handling a body specimen is described for particular use in the handling of fecal specimen which are to be treated with a stain for enhancing its visibility. The system includes dual optical viewing chambers mounted alongside of each other on a frame with appropriate tubing connecting ports of the viewing chambers to a liquid specimen supply and the satin supply. The stain supply is connected to one of the tubings leading to a viewing chamber so that the drawing action from a pump connected to ports on the other side of the viewing chambers can force an automatic mixing of the staining solution with one of the liquid specimen being drawn into one of the viewing chambers. Controls and techniques for operating the system are described.

21 Claims, 5 Drawing Sheets

APPARATUS AND METHOD FOR HANDLING FLUID SAMPLES OF BODY MATERIALS

PRIOR APPLICATION

This patent application claims the benefit of Provisional Patent Application Ser. No. 60/014,096, entitled FE-2 Theory Of Operation, filed Mar. 26, 1996 by Walter Greenfield, Mark J. Chiappetta and Todd M. Demafteo and assigned to the same assignee as for this application.

FIELD OF THE INVENTION

This invention generally relates to a method and apparatus for automating the viewing of a sample of body material and more specifically to the transfer of a prepared body material sample to a viewing chamber and subsequently to a disposal.

BACKGROUND OF THE INVENTION

U.S. Pat. Nos. 5,248,480 and 5,393,494 to Greenfield et al. describe an apparatus and method for drawing a fluid sample into a slide assembly for viewing through a microscope. The fluid is drawn from a container by way of a reversible pump. The fluid, such as a urine sample, is drawn in from the container through a glass slide and after viewing purged from the slide by reversing the pump so that it can draw flushing liquid back through the slide into the fluid sample container.

U.S. Pat. No. 3,352,280 describes an automatic stain apparatus for staining biological specimen. A dyeing apparatus is described in U.S. Pat. No. 4,025,393. An apparatus wherein a slide is moved to a staining station and then to a buffer station and thence to a rinsing station is described in U.S. Pat. No. 4,034,700.

These prior art techniques, other than the Greenfield patents, for the handling of samples either are too complex or involve physical exposure to the biological specimen being reviewed and are not readily suitable for a safe handling by the operator who evaluates the particular specimen in the slide.

SUMMARY OF THE INVENTION

With an apparatus and method in accordance with the invention an automatic handling and staining or other treatment of a prepared sample is obtained and a transfer into a slide assembly can be made so that the sample can be viewed through a microscope and evaluated without having the operator contact the specimen.

This is achieved with one apparatus in accordance with the invention, such as for the analysis of a fecal sample, by automating the transfer of the prepared fecal sample from a holding container to a novel, dual optical viewing chamber. With this dual chamber the microscopic analysis of the sample for intestinal helminth eggs and larvae, protozoan cysts, and coccidian oocysts is facilitated. The apparatus, identified as the FE-2, excels in the simplification and standardization of such biological examinations.

With an apparatus in accordance with the invention the sample is automatically treated with an appropriate chemical solution such a staining solution so that an operator can view an untreated sample in one chamber and a treated or stained sample in another adjacent chamber.

It is, therefore, an object of the invention to provide an efficient apparatus and method for automatic treatment and handling of a body material in a convenient, economic manner that is safe for the operator.

These and other objects and advantages of the invention can be understood from the following description of an illustrative embodiment of the invention as shown in the drawings.

DETAILED DESCRIPTION OF DRAWINGS

Figure 1:
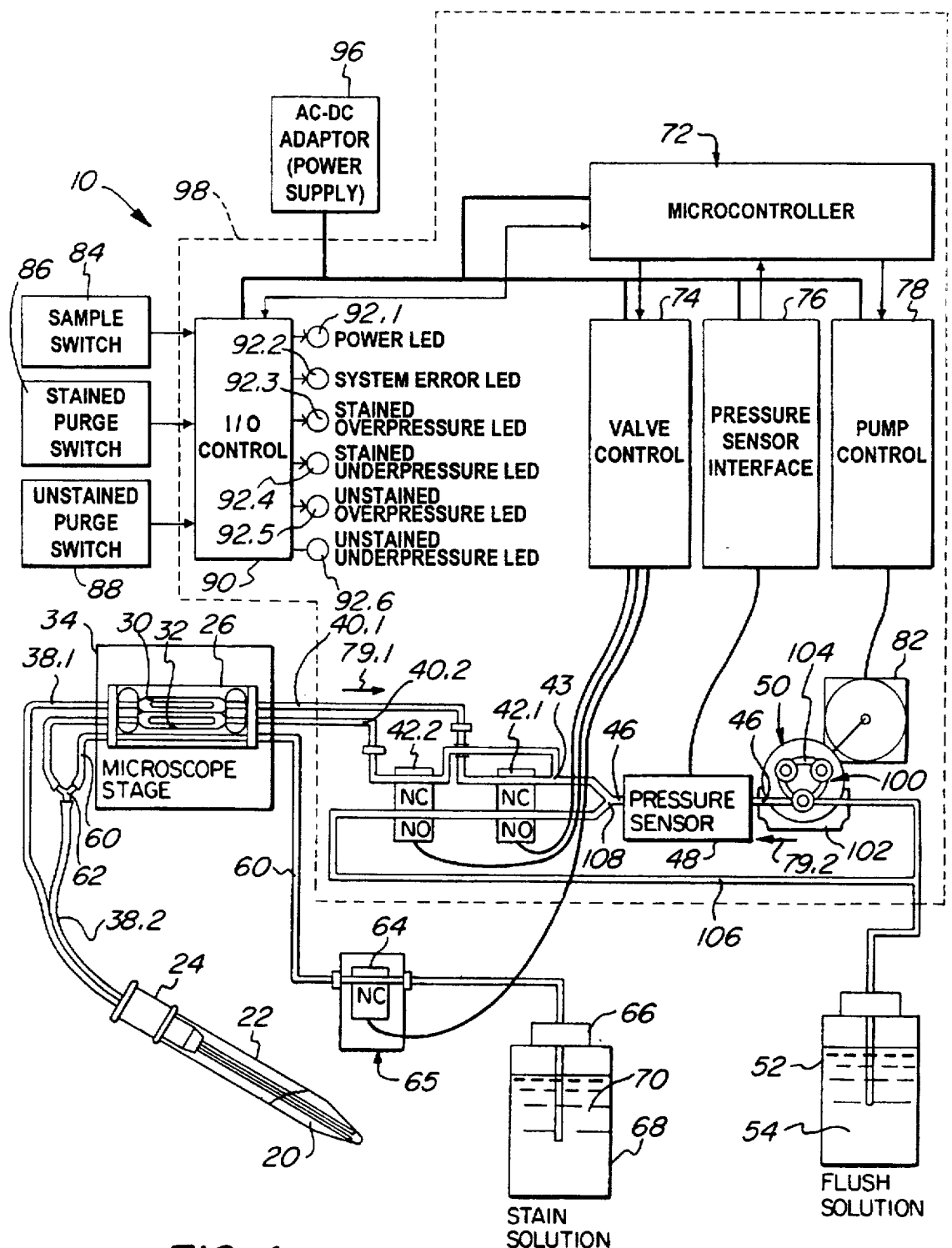
FIG. 1 is an overall block diagram of a system in accordance with the invention for use in the analysis of fecal specimen.
Figure 2:
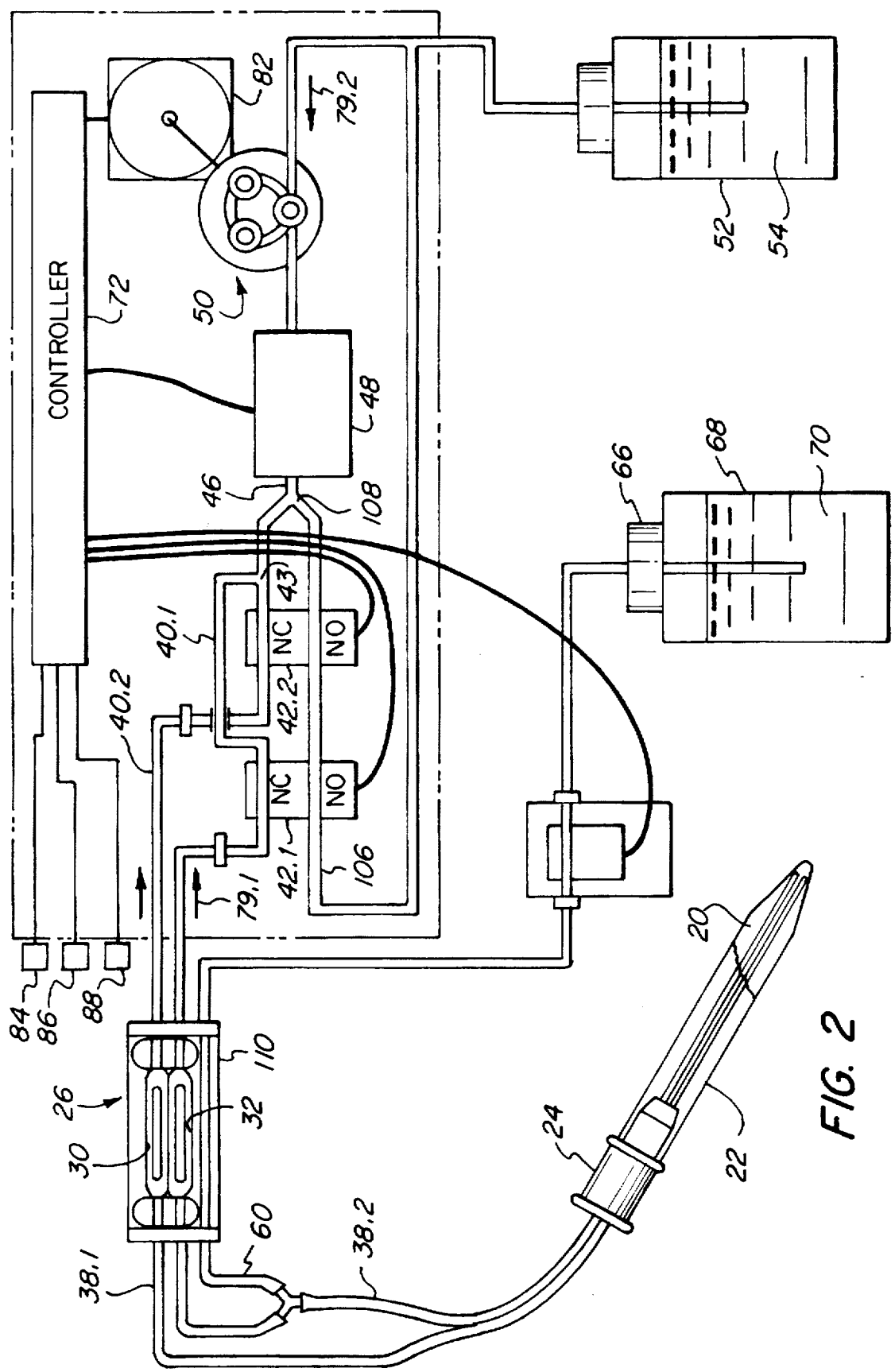
FIG. 2 is an enlarged view of a fluid flow section of the system shown in FIG. 1.
Figure 3:
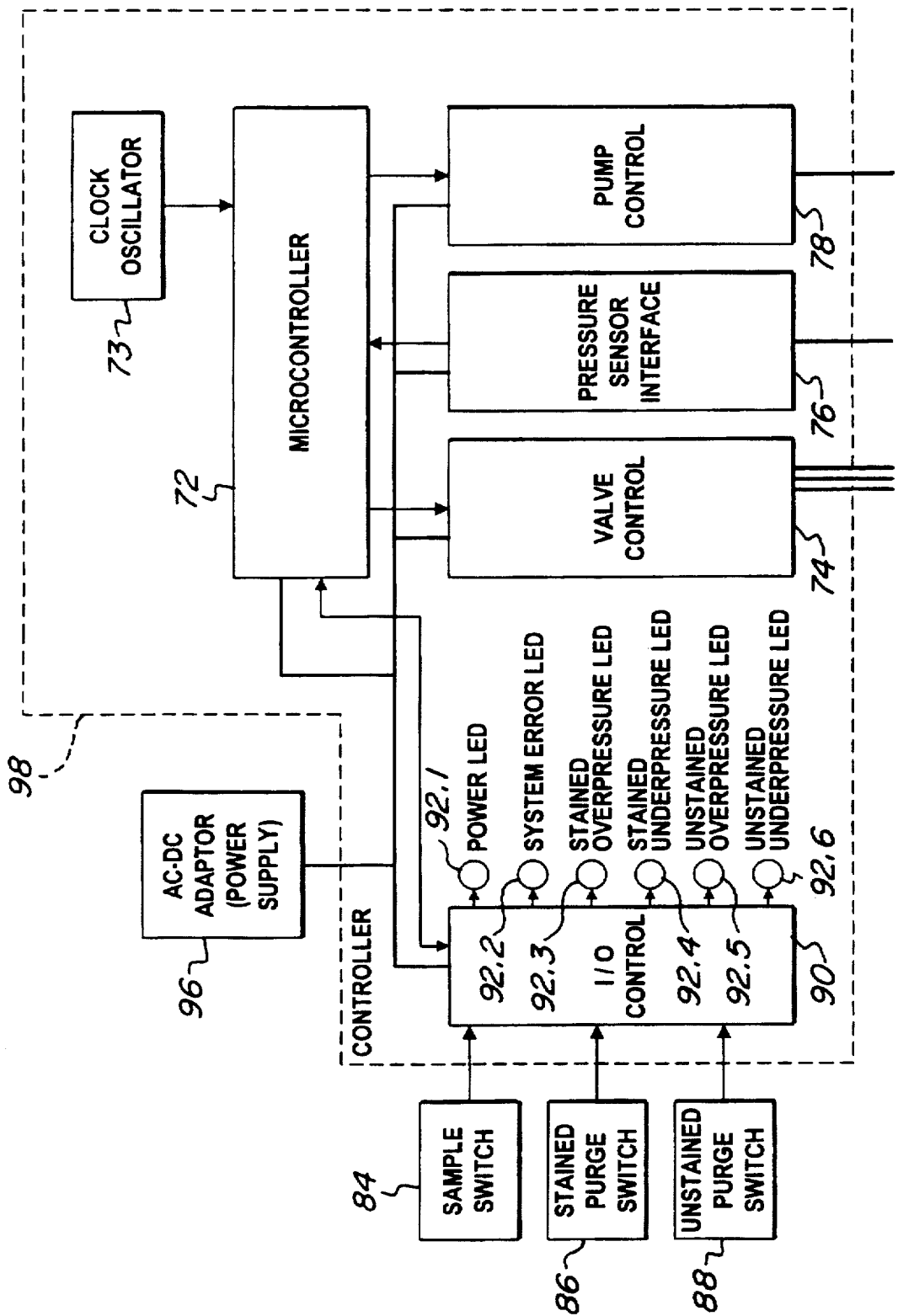
FIG. 3 is an enlarged view of a control segment of the system of FIG. 1.
Figure 4:
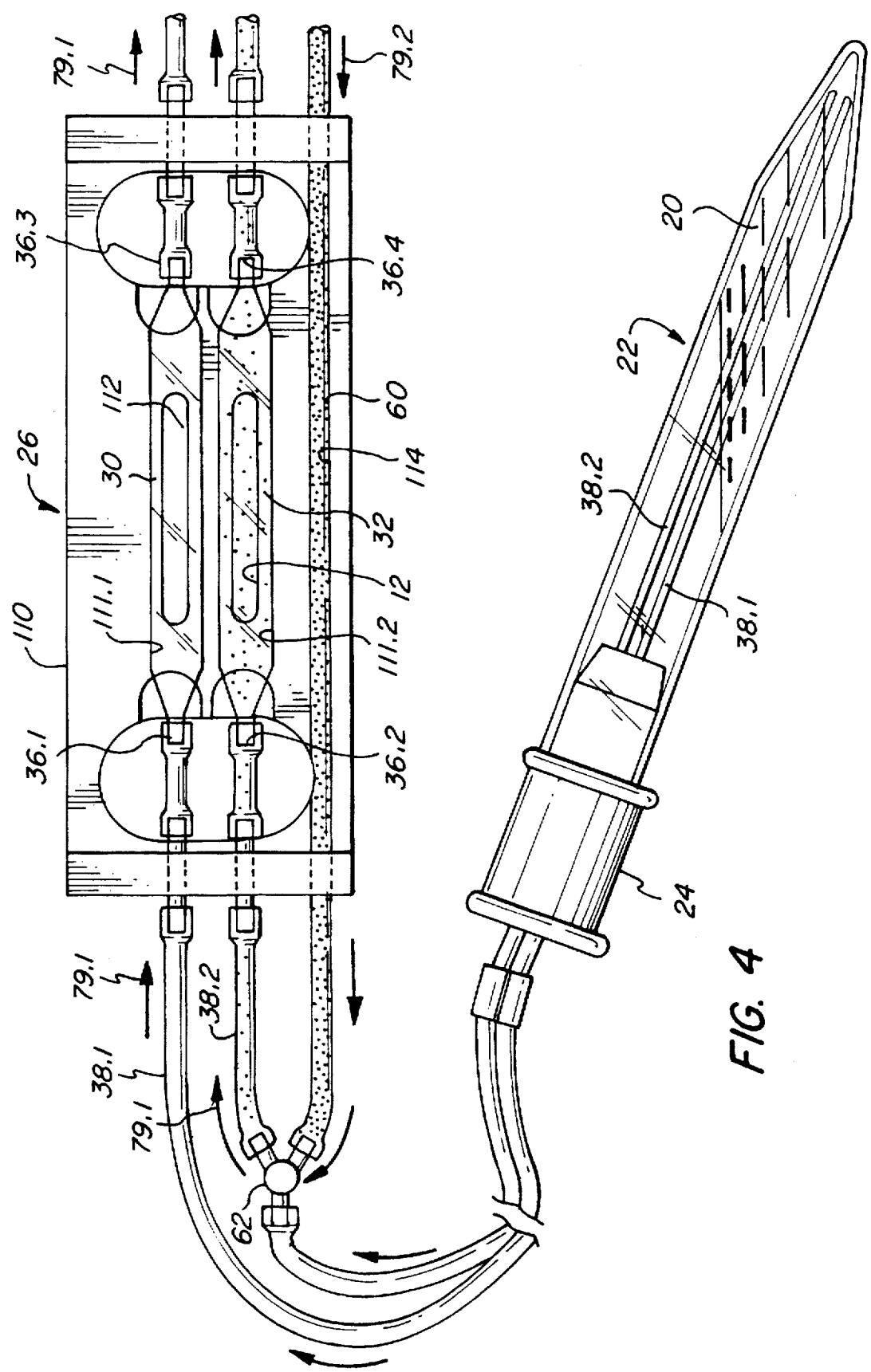
FIG. 4 is a plan view of a slide assembly in accordance with the invention and is an enlargement of a portion of the view in FIG. 1.

With reference to FIGS. 1–4 an apparatus 10 is shown with which a prepared fecal specimen 20 is drawn from a holding container 22 via a dual aspirator assembly 24 and transferred to a slide assembly 26 having dual optical viewing chambers 30, 32. The slide assembly 26 is of a flat configuration having a general shape as more particularly described in the aforementioned U.S. Pat. No. 5,393,494 to Greenfield et al. This patent is, therefore, incorporated herein by reference thereto subject to such modifications as are described herein.

Use herein of decimals serves to denote specific items with the numerals on the right side of the decimal point while reference to the numeral on the left side of the decimal refers to the same item, or items, in a general way.

The slide assembly 26 can be mounted to the stage of any standard, upright microscope 34 as described in the '494 Greenfield patent. The slide assembly's viewing chambers 30, 32 have end located ports 36.1–36.4, see FIG. 4. Ports 36.1 and 36.2 are coupled by tubings 38.1 and 38.2 to dual aspirator assembly 24 and extend into the specimen solution 20. Ports 36.3 and 36.4 are in turn coupled by tubings 40.1 and 40.2, via solenoid controlled pinch valves 42.1 and 42.2. Valve 42.1 is normally closed and valve 42.2 is normally open. The tubes 40 are joined at a junction 43 to merge into a single tubing 46. The tubing 46 in turn is passed through a pressure sensor 48 to a reversible peristaltic pump 50 and thence into a reservoir 52 containing a flushing liquid 54.

A treating liquid supply tube 60 is connected to junction 62 in tubing 38.2 so as to provide a mixing point, preferably ahead of the viewing chamber 32, for a treating solution into the specimen containing tube 38.2. The treating solution is obtained by passing tubing 60 through a normally closed solenoid controlled pinch valve 64 and connecting the tubing 60 to an aspirator assembly 66 attached to container 68 having a treating solution 70. The treating solution can be any suitable material useful for the treatment of specimen 20 to enhance its observation by a microscope and in the case of a fecal specimen can be a staining solution.

Operation of system 10 involves a microcontroller 72, which in turn controls a valve control 74 coupled to operate valves 42, and 64, senses overpressure conditions sensed by pressure sensor 48 and controls a pump control 78 coupled to drive a motor 82 connected to peristaltic pump 50. Activation of the system is begun with a sample switch 84 and completion of a visual analysis is followed by activating purge switches 86 and 88 to respectively purge the stain solution from tubing 40.2 and cleanse the junction 60 as described below. An input/output control 90 is connected to microcontroller 72 and operates suitable system status conditions by illuminating led's 92.1–92.6 for the conditions as noted in FIG. 1.

Operation of system 10 is initiated by actuation of the sample switch 84 by the user. Upon detecting this button push, the microcontroller 72 commands the valve control circuitry 74 to open both of the internal pinch valves 42.1 and 42.2. This opens both of the normally-closed hydraulic systems represented by tubes 40.1 and 40.2. The microcontroller 72 also actuates motor control 78 so as to activate the pump 50 in a sample direction, as indicated by arrow 79.1, as will cause an aspiration of specimen liquid 20 from container 22. As the specimen 20 begins to enter the dual optical viewing chambers 30, 32, another pinch valve 64, which is housed in an enclosure 65, external to the apparatus, is activated.

This activation opens yet another portion of the hydraulic system and allows transfer of a stain solution 70 from its holding container 68, to Y-fitting 62, where the stain naturally mixes with some portion of the fecal specimen 20 and enters the optical viewing chamber 32 of the dual optical viewing chamber assembly 26. The dual optical viewing chamber assembly 26 will from here on out be referred to as the slide assembly 26.

While a portion of the fecal specimen 20 is being mixed with the stain solution 70 and drawn into chamber 32 of the slide assembly 26, another portion of the specimen is simultaneously drawn unmixed into the other viewing chamber 30 of the slide assembly 26. This procedure is made possible by maintaining two, isolated hydraulic systems within the slide assembly 26. Once both viewing chambers 30, 32 of the slide assembly 26 have been respectively filled with specimen 20 and the specimen/stain mixture, both internal pinch valves 42.1 and 42.2 are closed by the valve control 74 and an operator can begin the actual visual analysis of the stained and unstained portions of the specimen.

While the analysis of the unstained portion of the specimen is first performed, the specimen 20 in the other viewing chamber 32 of the slide assembly 26 continues to react with the stain causing clinically significant, but normally transparent matter to take on color thus making it easily visible under microscopic examination. Once the analysis of the unstained portion of the specimen 20 is complete, it can be flushed out of its chamber, through half of the dual aspirator assembly 24, and either back out into the original holding container 22 or into another waste container followed by a larger volume of flush solution 54.

This purge operation is initiated by the assertion of the unstained purge switch 88 by the user. The purging of the unstained portion of the specimen is performed without disturbing the stained portion of the specimen, by opening the unstained system pinch valve 42.1, and keeping the stained system pinch valve 42.2 closed. The purging action is obtained by activating the motor with pump control 78 so that the pump is operated in a reverse flush direction, as indicated by arrow 79.2, causing a flow of flushing liquid 54 to move through the tubing 46 into tubing 40.1 and thence into container 22.

The stained portion of the specimen can then be analyzed in an identical method as with the unstained specimen. Once the examination of the stained specimen is complete, it also can be flushed from its viewing chamber 32 of the slide assembly 26, out through the other half of the dual aspirator assembly 24 and either into its original holding container 22 or into another waste container also followed by a larger volume of flush solution 54. This operation is initiated by assertion of the stained purge switch 86 by the user and results in a reversal of pump 50 so as to send flushing liquid 54 through tubing 40.2 towards container 22.

During the stained specimen purge cycle, the unstained system pinch valve 42.1 remains closed and the stained system pinch valve 42.2 opens after the stained specimen has passed beyond the Y junction 62. The normally closed external pinch valve 64 is then opened. The peristaltic pump motor 30 is operated to pump in the direction of arrow 79.1 to draw a small volume of stain back into or towards viewing chamber 32 of slide assembly 26. This action cleans out any residual matter that may have gotten trapped in the Y-fitting during the sample cycle.

The external pinch valve 64 then closes and peristaltic pump 50 resumes purging of the stained hydraulic system by pumping flushing solution from supply 52 through the viewing chamber 32. While the stained specimen is flushed from its hydraulic system, the results of the analysis can be recorded. Upon completion of this flushing operation, the apparatus is ready to draw the next fecal specimen.

The main electrical portion of system 10 receives electrical power from either a regulated or unregulated AC-DC wallmount adapter 96, or a 12 Vdc battery, or any other direct current source capable of providing a minimum of 1.5 A of current while maintaining a 12 V potential difference. The normally-closed pinch valve 64, which is external of the system enclosure 98, is powered from a regulated 12 Vdc source within the system workstation's main enclosure.

Inside the main enclosure 98 reside two, printed circuit boards which contain circuitry for controlling the three pinch valves 42.1, 42.2, and 64, pressure sensor 48, and peristaltic pump 50, which is driven by a unipolar DC stepper motor 82. Also included is circuitry for communication with the human operator. From this point on, these independent electrical circuits will be referred to as valve control 74, pressure sensor interface 76, pump control 78, and input/output control 90. These circuits both receive power from the wallmount adapter 96, and communicate independently with internal microcontroller 72. The microcontroller 72 requires a clock oscillator signal source 73, see FIG. 3, and which serves the function as an incremental time reference for successive operations.

The internal hydraulic system of system 10 consists of a reversible, peristaltic pump assembly, two 3-way pinch valve assemblies 42.1, 42.2, and a pressure/vacuum sensor 48. The peristaltic pump assembly is comprised of a three-rotor impeller 100 mounted directly to the shaft of a reversible, unipolar stepper motor 82, a stainless steel tube mounting bracket 102, and a section of elastomeric tubing 104 in communication with tube 46 and which is stretched a calibrated distance between two, forked ends of the tube mounting bracket 102.

Total control of the peristaltic pump assembly resides with the pump control circuitry 78. This circuitry can alter the angular velocity and direction of the pump impeller 50 to comply with desired flow rate commands sent to it by the workstation's microcontroller 72. The control of this hydraulic system is what is commonly referred to as "closed-loop". The term "closed-loop" most accurately describes the fact that the microcontroller 72 issues a command to the pump control assembly 78, which responds by energizing the individual coils or phases of the unipolar stepper motor 82 in such a manner to turn the peristaltic pump impeller 50 in a direction and angular velocity to achieve a flow rate which is appropriate for the operation underway. Feedback is then obtained by the microcontroller 72, polling the pressure sensor interface circuitry 76, which reads the pressure sensor 48, to determine the sign and magnitude of the actual pressure within the hydraulic system.

The microcontroller 72 then uses this data along with previously collected data to calculate the approximate flow rate of the liquid in the system. If the commanded flow rate varies from the actual flow rate, then an updated command is sent to the pump control circuitry 78, which will work towards eliminating the difference between these two values.

If during the pressure sensor polling operation, the microcontroller 72 detects one of the preprogrammed error conditions such as overpressure or underpressure in either the stained or unstained portions of the hydraulic system, the operation is ceased, the system error light-emitting diode 92.2 is illuminated along with another appropriate error-indicating LED 92, and an audible warning indicator is pulsed. Along with the system error LED 92.2, four other light indicating errors are provided such as are labelled in FIGS. 1 and 3 with a stained overpressure 92.3, a stained underpressure 92.4, an unstained overpressure 92.5, and unstained underpressure 92.6, to inform the operator of such a fault condition.

To clear an error-indicating LED 92 and stop the audible warning indicator from pulsing, the operator must press and release the unstained purge switch 88. However the system Error LED 92.2 will remain illuminated until the actual error condition is remedied. Until all errors are cleared, the microcontroller 72 will not permit the operator to sample another fecal specimen 20.

The pinch valves 42 are dual acting in that they each act on a tubing 40 with a normally closed pinch section and when this section is opened another tube 106 is pinched closed. Tube 106 provides a parallel connection from a junction 108 to flushing solution container 52 so as to enable the flushing fluid to be pumped back into the container 52 in case one of the pinch valves 42 malfunctions.

The slide assembly 26 includes viewing chambers 30, 32 which are each similar to the transparent glass enclosures as shown and described in the aforementioned and incorporated by reference U.S. Pat. No. 5,393,494 in its FIGS. 17–22. The slide assembly 26 of the instant invention has a frame 110, see FIG. 4 herein, with a pair of elongate side by side parallel recesses 111.1 and 111.2 in which the glass enclosures 30, 32 are placed and retained. Each glass enclosure 30, 32 overlies an opening 112 in the frame 110 to enable a back lighting for enhanced viewing. In addition, the frame 110 has a groove 114 to receive the tube 60, though this could be passed around the frame. The junction 62 is formed of suitable plastic or glass material.

Figure 5:
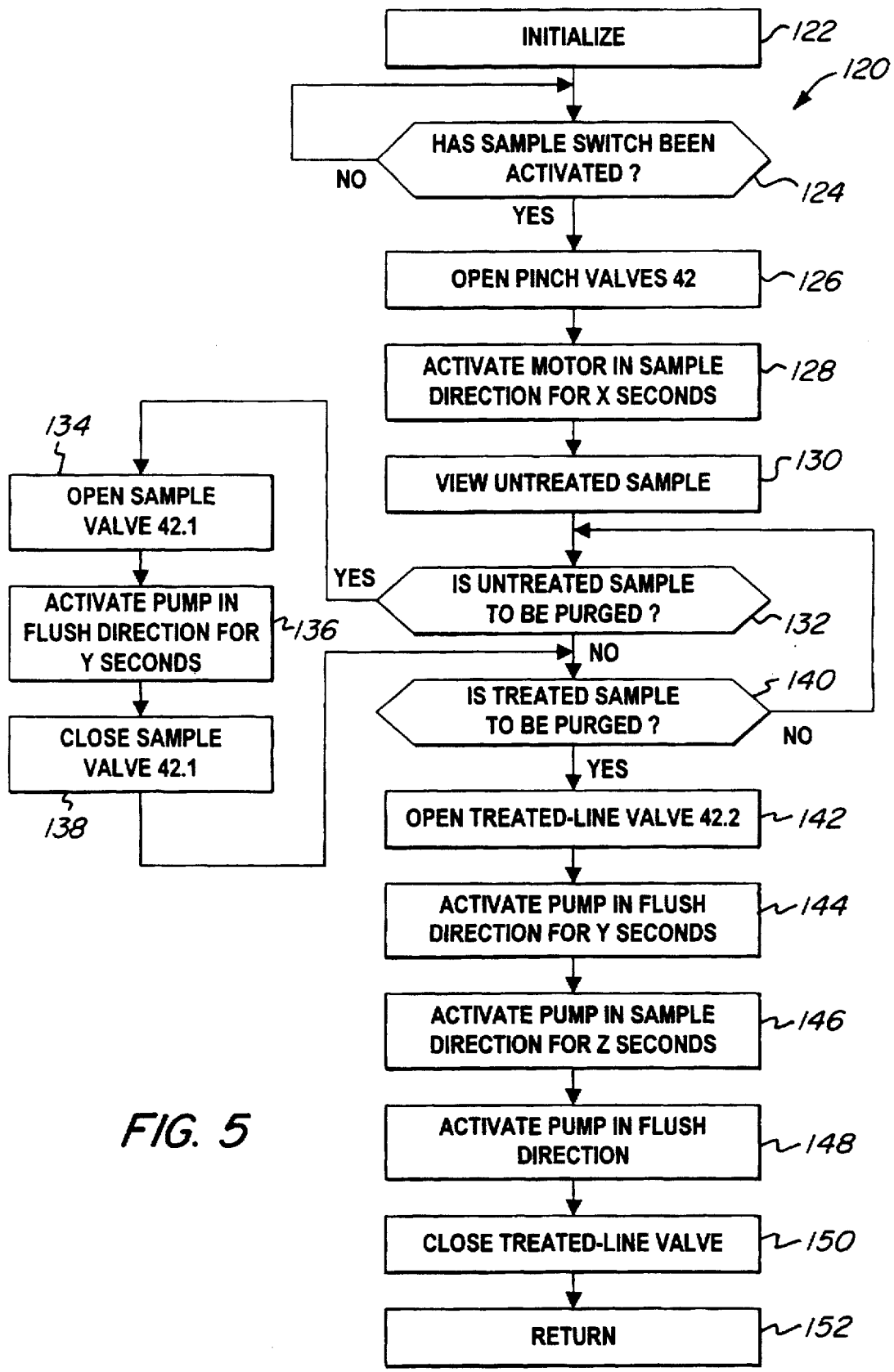
FIG. 5 is a flow diagram showing the described operation of the fluid handling system in accordance with the invention.

FIG. 5 illustrates a simplified flow chart 120 for the operation of the microcontroller 72. At 122 the controller is initialized with the appropriate signals such as the durations for the respective pump cycles, x seconds to draw a sample, y seconds for flushing the samples from the slide assembly 26 and z seconds to draw a cleansing sample of the staining solution. Other initial values are stored as well and the various controls are place in their respective reset conditions.

At 124 a test is made whether the sample switch 84 has been activated. If so the pinch valves 42 are opened at 126 and the motor activated at 128 in the sample direction for a sufficient time to draw a sample through the slide assembly 26 but without drawing the samples so far as to introduce them into the flushing solution supply 52. The samples including the sample to be stained are then reviewed at 130 as described above.

A test is then made at 132 whether the untreated sample is to be purged, actually sensing whether switch 86 has been activated. If so, the sample valve 42.1 is opened at 134 if it had been closed, but not the treating line valve 42.2, and the pump 50 activated at 136 in a flush direction 79.2 for a sufficient time to send flushing fluid through tube 40.1 and flush the sample into container 22. The sample valve 42.1 is then closed at 138 and a test is made at 140 whether the stained sample is to be purged, a test as to whether switch 88 has been activated.

If the treated or stained sample is to be purged, the treated line valve 42.2 is opened at 142 and the pump activated in the flushing direction at 144 for y seconds, enough to assure that the sample is flushed from the slide assembly and into the container 22. The pump is then, at 146 operated a short time to draw a staining solution into tubing 40.2 sufficient to use it for flushing of the junction 62. The pump is then reactivated at 148 in the flushing direction to purge the treating solution back into container 22. After closing treating line valve 42.2 at 150 a return is made at 152 to step 124 to enable another fecal specimen sample to be taken and reviewed as described.

Having thus described one embodiment in accordance with the invention its advantages can be appreciated. Variations from the described embodiment can be made without departing from the scope of the invention as to be determined from the following claims.

What is claimed is:

1. An apparatus for analyzing a body fluid specimen held in a first container and using a treating fluid retained in a second container to enhance the observation of the fluid specimen, comprising:

a slide assembly having first and second separate fluid specimen retaining optical viewing chambers; said viewing chambers each having first and second ports;

a pump having a first port and a second port;

first tubing means effectively coupling the first port of the pump to the first ports of the viewing chambers of said slide assembly;

a fluid mixing function;

second tubing means for coupling the second port of one of the viewing chambers through said fluid mixing function to both said fluid specimen in said first container and to said treating fluid in said second container;

third tubing means for coupling the second port of said second viewing chamber to the specimen in said first container;

whereby, in response to a pumping action of said pump from its first port to its second port, fluid specimen is drawn from said first container to be mixed by said mixing function with said treating fluid drawn from said second container to deliver a treated specimen fluid into said first viewing chamber and provide a fluid specimen for viewing in said second viewing chamber.

2. The apparatus as claimed in claim 1 wherein said first tubing means further comprises:

a first conduit and a second conduit interconnecting said second ports of the first and second viewing chambers to said pump and first valve means interposed in said respective first and second conduits for enabling individual control of fluid flow there through.

3. The apparatus as claimed in claim 2 wherein said first and second conduits are operatively coupled to each other at a junction located between said first valve means and said pump.

4. The apparatus as claimed in claim 3 and further including a pressure sensor operatively disposed to sense pressures in said first and second conduits.

5. The apparatus as claimed in claim 4 and further including second valve means interposed between said second container and said fluid mixing *unction for inhibiting fluid flow from said second container during a flushing cycle of the viewing chambers.

6. The apparatus as claimed in claim 5 and further including a microcontroller and means for coupling the microcontroller to operate said first and second valve means and said pump.

7. The apparatus as claimed in claim 6 and further including a pressure sensor interface coupled between said microcontroller and said pressure sensor to provide pressure signals for operation of said microcontroller.

8. The apparatus as claimed in claim 1 wherein a flushing fluid supply is provided to cleanse the slide assembly and further including:

means for controlling the flow of said flushing fluid through said second ports of the viewing chambers to cleanse them in preparation for viewing of another fluid specimen.

9. An apparatus for analyzing a body substance held in a first container as a liquid specimen with a staining solution held in a second container and using a flushing liquid stored in a third container, comprising:

a slide assembly having first and second liquid specimen retaining optical viewing chambers; said viewing chambers having first and second ends;

first means for coupling first ends of said viewing chambers to said first container so as to enable liquid specimen to be passed into the viewing chambers;

second means for coupling the second container to a first end of one of said liquid specimen retaining optical viewing chambers to provide a staining solution therein mixed with said specimen solution;

third means for coupling the flushing liquid in the third container to the second ends of said first and second liquid specimen retaining optical viewing chambers;

means for controlling the flow of liquid specimen and said staining solution through said first and second viewing chambers so as to deliver an unstained liquid specimen for viewing in one of said viewing chambers and for causing a stained liquid specimen for viewing in said other viewing chamber; and means for controlling the flow of said flushing liquid through said second ends of the viewing chambers to cleanse them in preparation for viewing of another liquid specimen.

10. The apparatus as claimed in claim 9 wherein said first and second means include aspirator assemblies for operative attachment to respective first and second containers and wherein said means for controlling the flow of said liquid specimen and staining solution includes a pump operatively connected to said second ends of said first and second viewing chambers to draw liquid samples from said first and second containers into the respective viewing chambers.

11. The apparatus as claimed in claim 10 wherein the aspirator assembly attached to said second container having the staining solution is so operatively coupled that drawing action from said pump on the second end of said second viewing chamber causes a mixing of liquid specimen and said staining solution ahead of said second viewing chamber.

12. The apparatus as claimed in claim 11 wherein said pump is connected between said viewing chambers and said third container having said flushing liquid.

13. The apparatus as claimed in claim 12 wherein said third means includes first and second conduits coupling said second ends of the viewing chambers to said pump; and first and second remotely controllable valves operatively disposed in said first and second conduits to enable control over the flow there through.

14. A method for handling a specimen fluid stored within a container and requiring treatment with a treating liquid for viewing inside an optical viewing chamber, comprising the steps of:

drawing a first sample of the specimen fluid so as to pass through a tube into a first viewing chamber and, while the first sample is moving through the tube, having the drawing action of the first sample draw a sample of said treating liquid through a junction into said tube so as to form a mixture with the specimen fluid within the tube and while continuing said drawing step moving the mixture to the first viewing chamber for observation of the mixture therein.

15. The method as claimed in claim 14 and further including the step of:

while moving the first sample drawing a second untreated specimen sample from the container and moving it to a second viewing chamber located adjacent to the first viewing chamber.

16. The method as claimed in claim 15 and further including the steps of:

purging the first and second viewing chambers of said specimen sample by pumping a flushing liquid therethrough;

after said first viewing chamber has been purged drawing said treating liquid in an amount sufficient to cleanse a junction where said treating liquid is drawn into said tube; and pumping flushing liquid through said first viewing chamber and said tube to remove said treating liquid.

17. A slide assembly for holding a liquid specimen comprising:

a pair of elongate transparent extruded glass seamless enclosures, each enclosure having an upper transparent wall for viewing a liquid specimen and each enclosure having ports to enable the introduction and purging of fluid;

a slide assembly holder; said enclosures being mounted in side by side relation ship on said holder.

18. A slide assembly for holding a liquid specimen comprising:

a pair of elongate transparent extruded glass seamless enclosures each having an upper transparent wall for viewing a liquid specimen;

a slide assembly holder; said enclosures being mounted in side by side relation ship on said holder.

19. An apparatus for analyzing a body fluid specimen held in a first container and using a treating fluid retained in a second container to enhance the observation of the fluid specimen, comprising:

a slide assembly having a fluid specimen retaining optical viewing chamber; said viewing chamber having first and second ports; and a pump having a first port and a second port, first tubing means for effectively coupling the first port of the pump to the first port of the viewing chamber of said slide assembly;

a fluid mixing junction;

second tubing means for effectively coupling the second port of said viewing chamber through said mixing junction to both said fluid specimen in said first container and to said treating fluid in said second container so that said fluid mixing junction can mix treating fluid with specimen fluid when said pump draws fluid through its first port to its second port to transport a treated specimen fluid into said viewing chamber.

20. The apparatus as claimed in claim 19 and further including:

first valve means interposed between said fluid mixing junction and said second container for controlling flow of treating fluid during a purging cycle of said optical viewing chamber.

21. The apparatus as claimed in claim 20 wherein said second port of the pump is coupled to a flushing solution and further including: a microcontroller and means for coupling the microcontroller to operate said first valve means and said pump to sequence the operation so that said pump alternately draws a treated specimen fluid into said viewing chamber and flushes the latter with said flushing solution.

* * * * *